United States Patent [19]
Brauker et al.

[11] Patent Number: 5,807,406
[45] Date of Patent: Sep. 15, 1998

[54] POROUS MICROFABRICATED POLYMER MEMBRANE STRUCTURES

[75] Inventors: James H. Brauker; Laura A. Martinson, both of Lake Villa; Shmuel Sternberg, Northbrook; David Bellamy, Keilworth, all of Ill.

[73] Assignee: Baxter International Inc., Deerfield, Ill.

[21] Appl. No.: 320,199

[22] Filed: Oct. 7, 1994

[51] Int. Cl.⁶ ..................................................... A61F 2/02
[52] U.S. Cl. .......................... 623/11; 623/16; 433/201.1; 424/422; 424/423
[58] Field of Search .................... 623/11, 16; 433/201.1; 424/422, 423

[56] References Cited

U.S. PATENT DOCUMENTS

| | | | |
|---|---|---|---|
| 3,514,791 | 6/1970 | Sparks | 623/1 |
| 3,852,832 | 12/1974 | McGhan et al. | 623/8 |
| 4,553,272 | 11/1985 | Mears | 623/10 |
| 4,576,608 | 3/1986 | Homsy | 623/11 |
| 4,601,868 | 7/1986 | Radel et al. | 264/504 |
| 4,636,219 | 1/1987 | Pratt et al. | 623/22 |
| 4,976,738 | 12/1990 | Frey et al. | 623/16 |
| 5,314,471 | 5/1994 | Brauker et al. | 424/422 |
| 5,344,454 | 9/1994 | Clarke et al. | 623/11 |
| 5,348,788 | 9/1994 | White | 623/11 |
| 5,380,328 | 1/1995 | Morgan | 623/16 |
| 5,496,372 | 3/1996 | Hamamoto et al. | 623/16 |

FOREIGN PATENT DOCUMENTS

| | | |
|---|---|---|
| 0 159 034 A2 | 10/1985 | European Pat. Off. . |
| 0 359 575 A2 | 3/1990 | European Pat. Off. . |
| 0 566 427 A3 | 10/1993 | European Pat. Off. . |
| 0 647 439 A2 | 4/1995 | European Pat. Off. . |
| 607388 | 1/1994 | Japan . |
| WO 90/00888 | 2/1990 | WIPO . |
| WO 92/22336 | 12/1992 | WIPO . |

*Primary Examiner*—Paul B. Prebilic
*Attorney, Agent, or Firm*—McDonnell Boehnen Hulbert & Berghoff

[57] ABSTRACT

Polymer membrane structures are microfabricated from polyimide film by lithography or etching. The microfabricated structures have systematically varied dimensions and geometries conducive to implanting in host tissue and the promotion, when implanted, of new vascular structures.

2 Claims, 15 Drawing Sheets

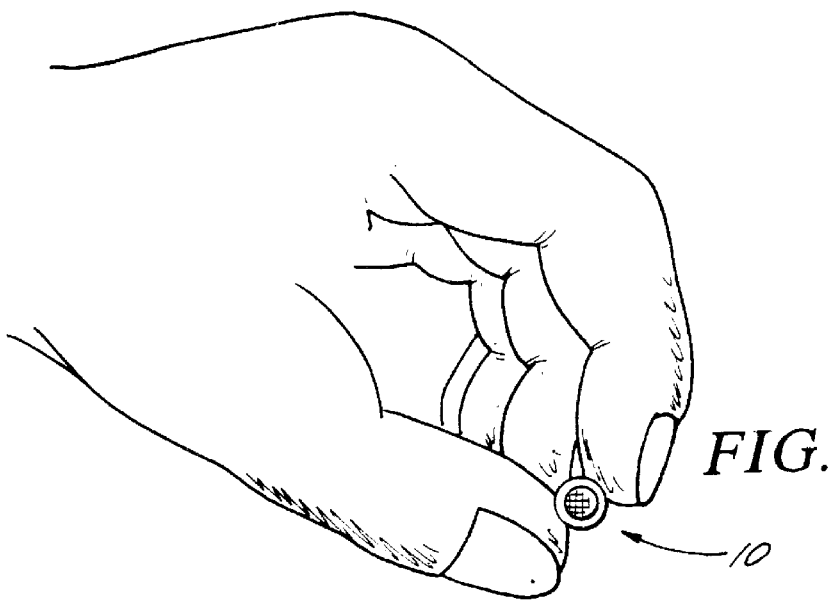
FIG. 1A
FIG. 1B
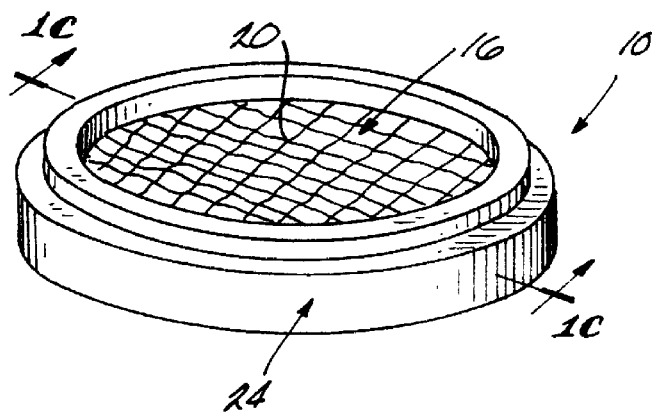
FIG. 1C
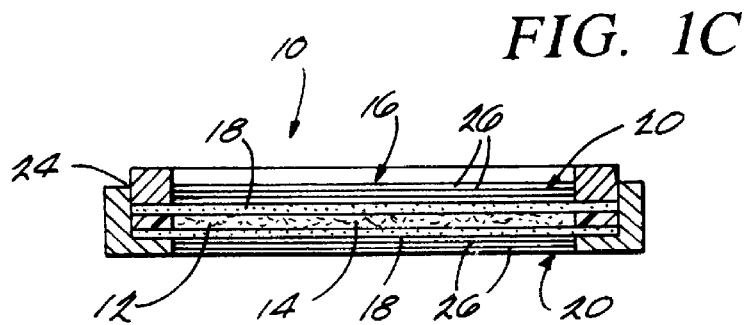

POROUS MICROFABRICATED POLYMER MEMBRANE STRUCTURES

FIELD OF THE INVENTION

The invention generally relates to systems and methods for implanting materials into body tissue. In a more particular sense, the invention relates to the structures and methods for implanting living cells in host tissue within porous membrane structures for achieving a desired therapeutic effect, such as, for example, the treatment of diabetes.

BACKGROUND OF THE INVENTION

Many diseases could be treated in a more physiologic fashion if tissue from lower animals could be transplanted into humans. However, the problem with discordant xenografting is hyperacute rejection of the transplanted tissue.

Immunoisolation, as its name implies, is the protection of transplanted organs, tissues, cells, etc. from attack by the host immune system. Isolation from the host immune system is accomplished by the use of a semipermeable membrane. Therefore, utilizing immunoisolation, it is theoretically possible to perform xenografts. This method has not worked well however, primarily because of the foreign body tissue response to the implanted polymer membrane.

The concept of immunoisolation was proposed by Chang nearly 30 years ago (see Chang, T. M. S.: Semipermeable microcapsules. *Science*, 146, 524–527 (1964). Since then many research groups have used immunoisolation membranes for transplantation of isolated tissues, in particular, pancreatic islets. The term bioartificial means the use of biologically active cells or organelles, but protected from immunological or other aggression by an artificial semiporous membrane. This membrane should permit the passage of low molecular weight substances, such as nutrients, electrolytes, oxygen, and bioactive secretory products, while excluding the passage of immunocytes, high-molecular weight proteins such as immunoglobulins, and other transplant rejection effector mechanisms.

The concept of immunoisolation and the bioartificial organ is particularly important due to the use of pancreas transplantation for the treatment of diabetes mellitus. Diabetes mellitus is the seventh leading cause of death in the United States, with an annual toll of about 35,000. It is estimated that 1 to 2% of the adult population have diabetes mellitus.

Even though the bioartificial pancreas (immunoisolated islets of Langerhans) has addressed the problems of transplantation of whole pancreas and unprotected human islets, it has created another problem, namely the tissue response to the artificial membrane surrounding the islets. The main reason for failure of these devices is the development of a fibrous foreign body capsule around the implant.

The foreign body reaction is characterized by inflammatory giant cells and macrophages at the tissue-membrane interface. The primary macrophage layer is normally overlain by many layers of fibroblasts in a collagen matrix oriented parallel to the surface of the implant. The fibrosis can be several hundred micrometers thick, and is typically avascular. This creates a diffusional barrier for nutrients and secretory products. The encapsulated tissue essentially "starves" and becomes necrotic, leading to failure of the bioartificial organ.

A major area of biomaterials research is concerned with addressing the tissue response to implanted materials. In particular, the fibrotic reaction developed against implanted polymer membranes is of primary concern regarding many implantable devices. Some evidence has indicated that the chemistry of the surface of the material is not the determining factor, but rather it is the microstructure of the interface which affects the tissue response.

Recently, studies by Brauker et al. with immunoisolation membranes have indicated that their vascularizing properties are dependent on the membranes microarchitecture (see Brauker, J., Martinson, L., Young, S., Johnson, R. C.: Neovascularization at a membrane-tissue interface is dependent on microarchitecture. Transactions of the Fourth World Biomaterials Congress Apr. 24–28, 1992 p. 685; Brauker, J., Martinson, L., Carr-Brendel, V. E., and Johnson, R. C.: Neovascularization of a PTFE membrane for use as the outer layer of an immunoisolation device. Transactions of the Fourth World Biomaterials Congress Apr. 24–28, 1992 p. 676; Brauker, J., Martinson, L., Hill, R., and Young, S.: Neovascularization of immunoisolation membranes: The effect of membrane architecture and encapsulated tissue. Transplantation 1:163,1992; and Brauker, J., Martinson, L. A., Hill, R. S., Young, S. K., Carr-Brendel, V. E., and Johnson, R. C.: Neovascularization of immunoisolation membranes: The effect of membrane architecture and encapsulated tissue. Transplantation Proceedings 24:2924, 1992).

Brauker et al. have observed that membranes of the same type of material, differing only in their microarchitecture, create a marked difference in biological responses when implanted in terms of the number of vascular structures near the host tissue-material interface.

Brauker et al. have characterized the difference as follows:

Membranes that did have close vascular structures allowed cellular infiltration, and had pores that were formed by membrane structures (strands or fibers) with a diameter of less than 5 $\mu$m, whereas membranes that did not develop close vascular structures had cavities with "plate-like" qualities, having diameters greater than 5 $\mu$m. Histological examination of the vascularizing membranes revealed that the invading inflammatory cells (of the host) had a rounded morphology, while the cells were flattened in the membranes that did not have close vascular structures.

The Brauker et al. hypothesis is that the membrane architecture dictates cellular morphology, and the rounded cells in turn secrete some, as yet unknown, trophic factors which promote the formation of vascular structures.

SUMMARY OF THE INVENTION

The invention provides layered porous polymer membrane structures formed by microfabrication. The microfabricated structures comprise precisely defined three-dimensional porous structures with chemical inertness and robust mechanical properties suitable for implantation in host tissue.

One aspect of the invention provides a porous structure for implanting in host tissue. The structure includes multiple layers of microfabricated polymer film, each layer having predefined geometric patterns of holes and intermediate spaces defining strands.

In a preferred embodiment, the porous structure forms a chamber to hold living cells while implanted in host tissue. In a preferred implementation, the geometric pattern in one of the layers differs from the geometric pattern in another one of the layers.

The inventors have found that, by stacking individual layers of polymer film microfabricated with different geometric patterns, a three dimensional interior architecture is created. The architecture emulates the geometry identified by Brauker et al. for promoting the growth of vascular structures near the interface between host tissue and the porous structure.

In a preferred embodiment, the membrane structures comprise layers of polyimide film with microfabricated geometric patterns of holes and intermediate strands. The structures include one layer having a first microfabricated geometric pattern sandwiched between two other layers having microfabricated geometric patterns different than the first geometric pattern. The first geometric pattern comprises holes having a cross dimension greater than about 20 $\mu$m spaced apart by strands less than about 5 $\mu$m. The other geometric patterns comprise smaller holes having a cross dimension equal to or less than about 20 $\mu$m spaced apart by smaller strands equal to or less than about 2 $\mu$m.

Another aspect of the invention provides a method of implanting living cells in host tissue. The method forms a chamber to hold living cells. The chamber has a wall structure that includes multiple layers of microfabricated film, each layer having predefined geometric patterns of holes and intermediate spaces defining strands. The method places living cells in the chamber and implants the chamber and living cells it contains in host tissue.

BRIEF DESCRIPTION OF THE DRAWINGS

FIGS. 1A and 1B are perspective views (FIG. 1A being scaled with reference to a human hand and FIG. 1B being enlarged) of an implant assembly that includes a porous membrane structure comprising multiple layers of polymer film material that embodies the features of the invention;

FIG. 1C is a side section view of the implant assembly taken generally along line 1C—1C in FIG. 1B;

Figure 2:
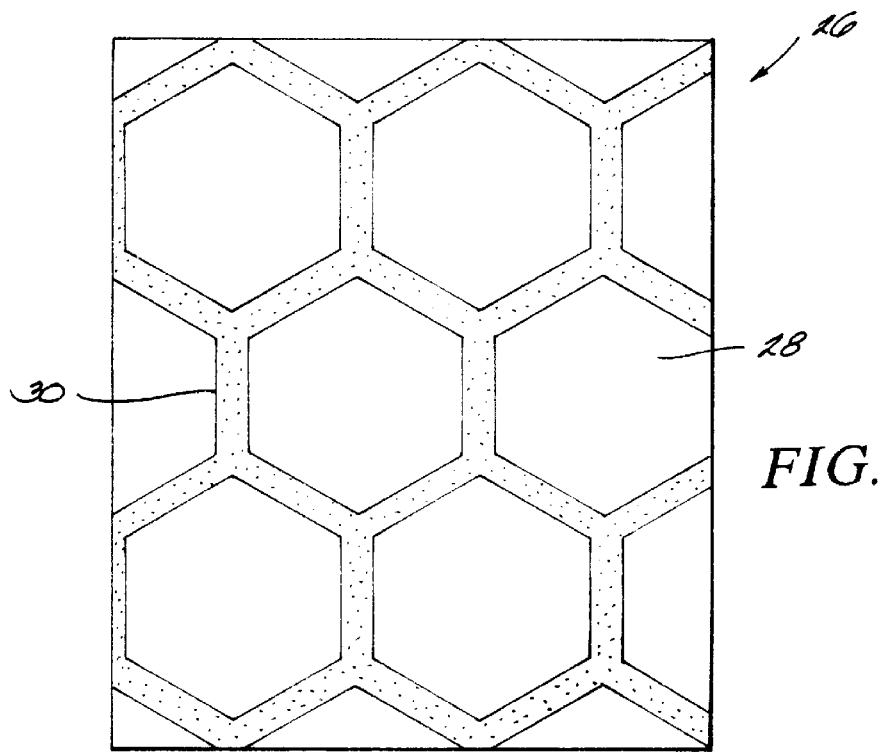
FIG. 2 is a top view of the geometric pattern of holes and strands that the outer porous layer of the membrane structure shown in FIG. 1 possesses.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIGS. 1A/B/C show an implant assembly 10 that embodies the features of the invention.

The assembly 10 forms a chamber 12 (see FIG. 1C) to hold living cells 14 while implanted in host tissue. The implanted cells 14 generate biological products that the host, because of disease or injury, cannot produce for itself. For example, the chamber 12 can carry clusters of pancreatic cells (called "islets"), which generate insulin for release into and use by a diabetic host.

In the embodiment shown in FIG. 1, the assembly 10 is carried within a hoop-like housing 24 (see FIGS. 1B/C). The details of construction of the hoop-like housing are disclosed in U.S. Pat. No. 5,344,454, which is incorporated herein by reference.

The assembly 10 forms a porous, life sustaining boundary 16 between the implanted cells 14 and the host. The porous boundary 16 includes a first porous region 18 immediately surrounding the chamber 12. The first region 18 has a pore size sufficient to block penetration into the lumen of the chamber 12 by host vascular structures. This penetration breaches the integrity of the boundary 16, exposing the implanted cells 14 to the complete immune response of the host. Generally speaking, pore sizes less than about 2 $\mu$m (i.e., 2 micrometers) will block the ingress of vascular structures. (As used in this Specification, "pore size" refers to the maximum pore size of the material. The practitioner determines pore size using conventional bubble point methodology, as described in Pharmaceutical Technology, May 1983, pages 36 to 42).

When the implanted cells 14 are from another animal species (i.e., xenografts), the pore size of the first region 18 must also be sufficient to prevent the passage of both inflammatory cells and molecular immunogenic factors from the host into the implant tissue chamber. As used in this Specification, "inflammatory cells" include macrophages, foreign body giant cells, and fibroblasts, and "molecular immunogenic factors" refers to molecules such as antibodies and complement. Pore sizes sufficient to block passage of both inflammatory cells and molecular immunogenic factors in humans lie in the range of about 0.015 micrometers. Of course, these pore sizes are also impermeable to vascular structures.

When the implanted cells are from the same animal species but having a different genetic make up (i.e., allografts), the pore size of the first region 18 usually must be sufficient to prevent the passage of only inflammatory cells from the host into the implant cell chamber. In allografts, molecular immunogenic factors do not seem to adversely affect the viability of the implanted cells. Still, some degree of tissue matching may be required for complete protection. Pore sizes sufficient to block passage of inflammatory cells in humans lie in the range of below about 0.8 micrometers. These pore sizes, too, are impermeable to vascular structures.

When the implanted cells are isografts (autologous implants of genetically engineered cells), the pore size must be sufficient only to prevent the isografts from entering the host, while also preventing ingress of vascular structures in the chamber 12.

The boundary 16 also includes a second porous region 20 overlying at least a portion of the first region 18. The second region 20 constitutes the interface with host tissue. The second region 20 has an architecture that promotes the growth of vascular structures in host tissue near the interface. Preferably, at least some of the near vascular structures lie within one cell thickness of the interface.

In this way, the porous boundary 16 associates itself with the host's biological system closely enough to transfer nutrients and wastes in support of the biological processes of the implanted cells 14. The porous boundary 16 also transfers the therapeutic products generated by the implanted cells 14 to the host.

According to the invention, the second region 20 comprises a porous membrane structure formed with multiple microfabricated layers of polymer film 26.

In the illustrated and preferred embodiment, each polymer film layer 26 (see FIG. 2) is made from photoimageable polyimide material. The film 26 is processed, using either negative photoresist techniques or etchable membrane fabrication techniques, to create predefined geometric patterns of holes 28 and intermediate spaces defining strands 30. (see FIG. 2).

The geometric patterns alternate between film layers 26 from smaller, more closely spaced hole patterns (with cross hole dimensions equal to or less than about 20 μm and strand dimensions typically about 2–3 μm) to larger holes with less closely spaced patterns (with cross hole dimensions exceeding 20 μm and upwards to about 50 μm and strand dimensions typically about 4–5 μm). The stacking of different geometric patterns creates an open, porous membrane structure having randomly positioned, interconnected cavities with minimum interior dimensions greater than about 5 μm formed by interconnected stands with minimum dimensions less than about 5 μm.

The preferred embodiment shows the porous membrane structure being used in association with a chamber for implanting living cells. Still, it should be appreciated that the porous structure embodying the features of the invention can be used in association with other implanted objects, like catheters, biosensing devices, and the like.

I. Selection of Polymer Film Material

The membrane structure for the second region 22 and its fabrication require a number of characteristics, including biocompatibility, ease of fabrication, the ability to create identifiable, three dimensional geometries, chemical inertness, and robust mechanical properties. Polyimide is one material that meets these requirements. Polyimide, commonly used as planarizing dielectric layers in microelectronics, is biocompatible, mechanically strong, and can be routinely microfabricated into patterns of precise geometries using lithographic techniques.

Polyimides are cyclic-chain polymers. They are characterized by the imide functionality, which is a cyclic secondary amine bound to two carbonyl groups, and may contain either aromatic or aliphatic groups in the main chain.

Polyimide can be synthesized using a two step method via the precursor poly(amic-acids) (see Sroog, C. E.: Polyimides. Progress in polymer science 16:561–694, 1991). In this method, the precursor of the imide moiety, poly(amic-acid), is formed by a polycondensation (addition polymerization) reaction of an acid dianhydride with a diamine. Diamines that can be used include 4,4'-diaminodiphenyl ether (DADPE), also known as oxydianiline (ODA); 4,4-methylene dianiline (MDA); and 4,4'-diaminobenzophenone (DABP). Dianhydrides that can be used include pyromellitic dianhydride (PMDA); 3,3',4,4'-benzophenonetetracarboxylic dianhydnde (BTDA); and 3,3',4,4'-biphenyltetracarboxylic dianhydnde BPDA).

Poly(amic-acid) is soluble in polar organic solvents such as N-methyl-2-pyrrolidone (NMP), dimethyl formamide (DMF), and dimethylsulfoxide (DMSO). Depending on the structure of the radicals attached to the imide group, polyimides can be aliphatic, alicyclic, or aromatic; and linear or three-dimensional, depending on the chain structure. Aromatic, linear polyimides are the most common, essentially because they have found wide practical application because of their high level of performance over a broad temperature range.

During the second step of the method, the poly(amic-acid) is converted to the polyimide at temperatures high enough to remove the solvent and initiate ring closure with intramolecular expulsion of water. The heat treatment described is known as "curing", and typically has a final temperature range of 300°–500° C. The completeness of the imidization reaction depends on the nature of the R and R' groups as well as the specific conditions of the imidization or cure.

After complete cure, polyimide is insoluble in virtually all common solvents including photoresist strippers. However, some hot bases, such as hydrazine, antimony trichloride, arsenic trichloride, concentrated sulfuric acid and fuming nitric acid, will dissolve polyimide films.

The biocompatibility of different polyimides has been examined for use in cochlear implants. The polyimides investigated included Hughes HR610, Dupont 2555, Hitachi PIQ and M.&T. 2056/5000. All resulted in very limited adverse tissue response (see Haggerty, H. S. and Lusted, H. S.: Histological Reaction to polyimide films in the cochlea. Acta Otolaryngol (Stockh) 107:13–22, 1989).

II. Design of Membrane Microstructures

Figure 3A:
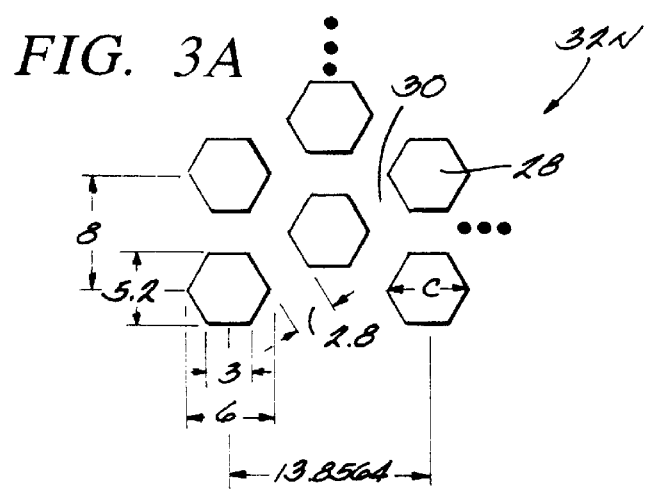
FIGS. 3A and 3B are representative mask designs that can be used to microfabricate the primary film layers of the porous membrane structure shown in FIG. 1.
Figure 4:
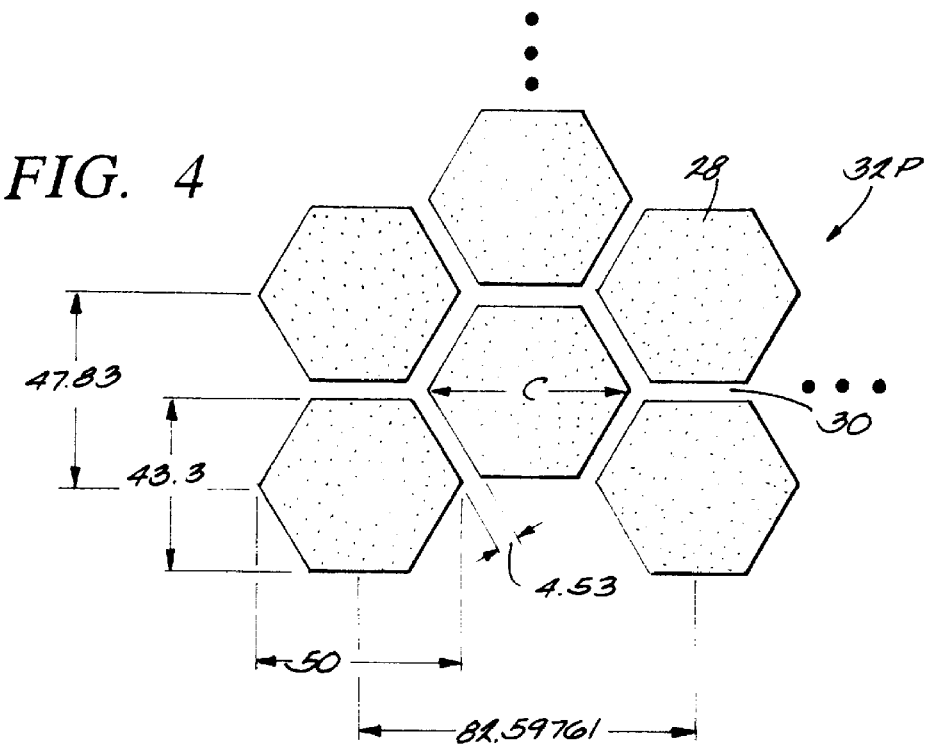
FIG. 4 is a representative mask design that can be used to microfabricate the spacer film layers of the porous membrane structure shown in FIG. 1.

FIGS. 3A/B and 4 show representative mask plate designs 32P and 32N for creating the desired geometric patterns on the polyimide films using known lithographic printing or etching techniques. So-called "negative mask" plates 32N (which FIGS. 3A/B show) can be used with light sensitive polyimide films (coated with negative photoresist material). So-called "positive mask" plates 32P (which FIG. 4 shows) can used for etchable polyimide films.

As FIGS. 3A/B and 4 show, the mask plate designs 32P and 32 N preferably use a "honey comb" pattern. The pattern has hexagonal holes 28. A hexagonal geometry achieves a high packing density and, therefore, a high porosity membrane.

The mask plate pattern 32 itself defines a planar surface geometry, i.e., the two dimensional horizontal x-y plane of the microstructure. The z-dimension (vertical plane) of the microstructure is defined by the thickness of the polyimide film 26. In the illustrated and preferred embodiment, individual films 26 having a thickness of about 2 μm are layered on top of each other to build vertical height in the z-direction, which can range from about 4 μm (i.e., two layers) to 14 μm (i.e., 5 or more layers).

FIG. 3A shows a mask plate design with hexagonal holes with cross dimensions (indicated by arrows C) which measure about 6 μm. The strands (i.e. the spaces between the holes) measure about 2.8 μm. This pattern creates a film that can be identified as a 6 μm/2.8 μm (hole dimension/strand dimension) structure. The nominal dimensions are shown (in μm) in FIG. 3A.

Figure 3B:
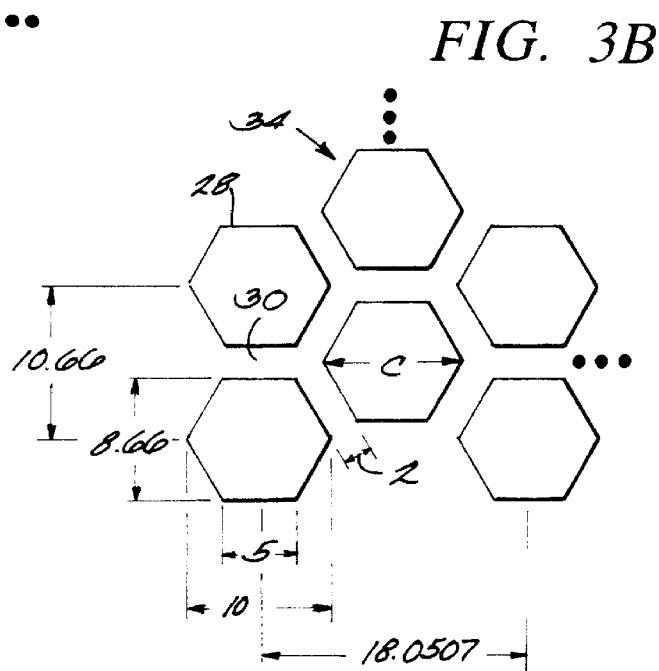

FIG. 3B shows another mask plate design based on this geometry having holes with cross dimension (again indicated by arrows C) of 10 μm and 2 μm strands. This pattern creates a film having a 10 μm/2 μm structure, using the nomenclature of the preceding paragraph. The nominal dimensions are shown (in μm) in FIG. 3B.

Each design shown in FIGS. 3A and 3B is intended to fit a one cm square area. Therefore, the interhex strand spaces are actually slightly less than 2.8 and 2 μm, but the difference is negligible (i.e. less than 0.01 μm). The smallest strand size that can be achieved is approximately 1.5 μm, being limited by the contact printing lithographic process and wavelength of the ultraviolet light. Inherent shrinkage of the polyimide film can occur during processing (as described below) and is beneficial, because it can reduce the stand size below that attainable strictly by the contact lithographic process.

When layers of film mirroring the hexagonal mask plate design shown in FIGS. 3 A and B are stacked on top of each other, the vertical pattern of the strands and holes in the microstructure emulate a three dimensional fibrous membrane structure of interconnected fibers (i.e., the vertical registration of stacked strands) forming interconnected interior cavities (i.e., the overlaying of the vertically stacked holes).

According to the invention, an open membrane structure made according to the teachings of Brauker et al.—having interconnected cavities with x, y, and z dimensions greater than 5 μm formed by interconnected stands with y dimensions less than 5 μm—is emulated in a stacked microfabricated film structure by including spacer film layers having large diameter holes (i.e., over about 20 μm and upwards to about 50 μm) than the 6 μm/2.8 μm and 10 μm/2 μm primary film layers already described.

FIG. 4 shows a mask plate design 32 for a spacer layer having 50 μm holes and 2 μm strands. The nominal dimensions are shown (in μm) in FIG. 4.

Like the designs shown in FIGS. 3A/B, the design shown in FIG. 4 is intended to fit a one cm square area. This pattern creates a spacer film having a 50 μm/2 μm structure.

According to the invention, the spacer layers having the design shown in FIG. 4 with larger diameter holes are alternated with the polyimide films having the design shown in FIGS. 3A or 3B with the smaller diameter holes. The layers of primary polyimide film and polyimide film spacers are stacked with random alignment to create an open membrane structure, as will be described in greater detail later.

In a preferred implementation, the mask designs shown in FIGS. 3 and 4 were layered out with an AutoCAD™ system. Each 1 cm² area was magnified by 10×, i.e. approximately 0.1 cm×0.1 cm areas of the final device. After file conversion, reticle plates were made on a GCA MANN 3600F pattern generator. The reticle (5" plate) was placed in the GCA MANN 3696 stepper which has optics that reduce the image 10×, and stepped across the mask (4" plate) in such a way as to make nine 1 cm² patterns.

The plates were soda lime glass plates covered with 5000 Å of low reflective chrome, and 5000 Å of Shipley™ Microposit™ AZ1350J photoresist (supplied by Nanofilm Inc.). After development the exposed plates were etched with CEN-300 micro-chrome etchant (Microchrome Technology Inc.) for 40 seconds. The process was completed with removal of the photoresist.

Both clear field and dark field versions of the mask plates were made, so that both negative acting polyimide and positive acting photoresist could be used for the creating the microstructures.

III. Preparing the Polyimide Structures

A. Microfabricating the Film Layers

In a preferred implementation, the following polyimides film materials were used in making microfabricated membrane structures that embody the features of the invention:

Light Sensitive Films

Amoco Ultradel™ 7501 (U7501): The exact chemical structure of these polyimides from Amoco Chemical Company (Naperville, Ill.) is proprietary. However, it is an inherently light sensitive, preimidized, benzophenone (BTDA) based fluorinated polyimide. The solvent system for this polyimide is gbutyrolactone.

OCG Selectiplast™ HTR3-100 (HTR3-100): The HTR3 series of polyimides from OCG Microelectronics (West Paterson, N.J.) are a PMDA/ODA based polyimide which has a sensitizer molecule providing light sensitivity. The exact chemical formulation of the sensitizer molecule is proprietary. The solvent system used for this polyimide is cyclopentanone.

Etchable Film

Amoco Ultradel™ 4212 (U4212): This is an etchable material with a chemical structure of a 4,4' hexafluoro-isopropylidene-bis pthalic anhydride (HFDA) and 4,4'-bis (4-aminophenoxy)biphenyl (APBP). The solvent system used for this polyimide is 2-methoxyethylether.

Figure 5A:
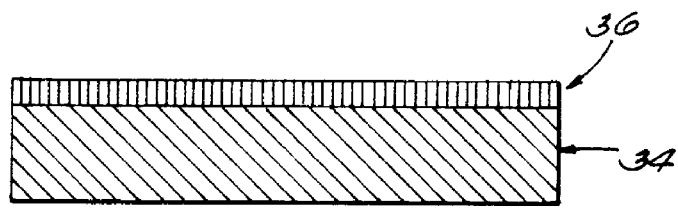
FIGS. 5($a$) to (5($c$)) are schematic views of the process of microfabricating the primary and spacer layers of the porous membrane structure using light sensitive polyimide film.
Figure 6A:
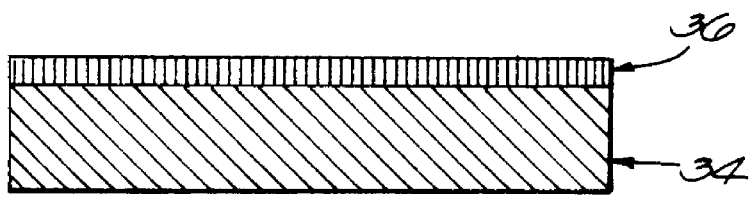
FIGS. 6($a$) to 6($e$) are schematic views of the process of microfabricating the primary and spacer layers of the porous membrane structure using etchable polyimide film.

FIGS. 5A/B/C show the steps of the fabrication process for the light sensitive polyimide films, for which the negative mask is used to create the desired microstructure. FIGS. 6A/B/C/D/E show the steps of the fabrication process for the etchable polyimide films, for which the positive mask is used to create the desired microstructure.

In a preferred implementation of each fabrication process, substrates 34 comprising two inch diameter silicon wafers were cleaned for 10 minute in Summa™ clean in an ultrasonic bath at 30° C., followed by a 5 minute deionized water (DI) rinse and blown dry in nitrogen. A steam oxide was grown at 1100° C. to a thickness of approximately 0.5 μm. This forms the sacrificial layer 36 used for later removal of the polyimide films from the substrate wafers (see FIG. 5A and FIG. 6A).

The oxidized substrate wafers are cleaned with filtered isopropanol and then coated with diluted adhesion promoter.

For the light sensitive film, the adhesion promoter was Amoco, Ultradel™ A200 (3-aminopropyltriethoxysilane). The adhesion promoter was diluted 1:2000 with mentanol and water. The adhesion promoter was spin coated at 5000

RPM on the oxidized substrate wafers, followed by a 30 second hot plate bake at 100° C. to remove moisture.

For the etchable film, OCG adhesion promoter (some type of aminosilane) was diluted 1:9 (QZ3289:QZ3290) (QZ3290 is ethanol). The adhesion promoter was likewise spin coated at 4000 RPM on the oxidized substrate wafers, followed by a 20 second hot plate bake at 110° C.

Figure 5B:
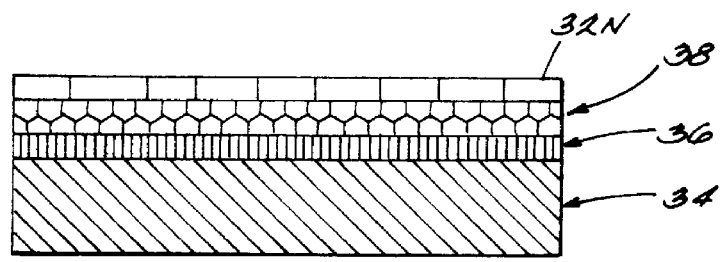
Figure 6B:
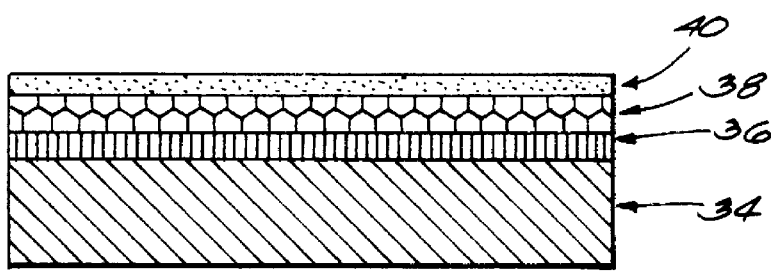

The polyimides 38 were then spin coated upon the substrates. The coated substrates were prebaked on a hot plate (Fairweather Inc., Thermal Ace, SantaClara, Calif.), fitted with vacuum ports for hard contact bake (see FIG. 5B and FIG. 6B).

Figure 6C:
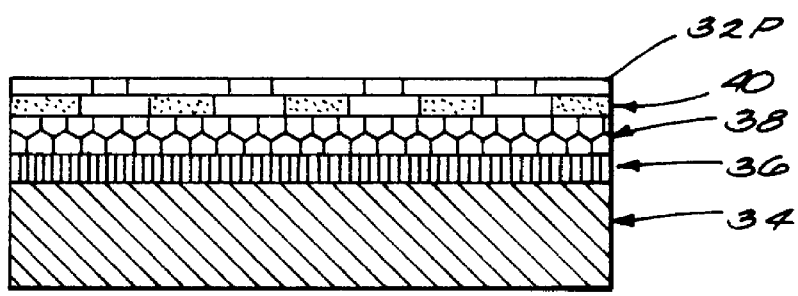
Figure 6D:
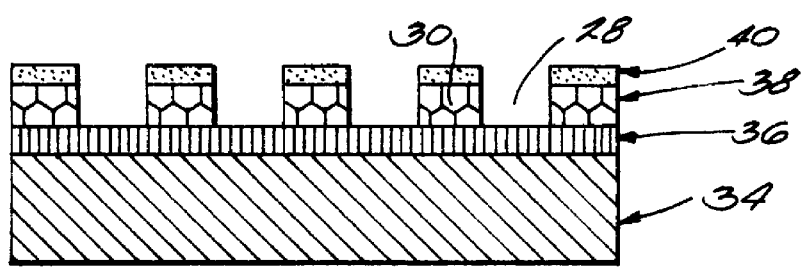
Figure 6E:
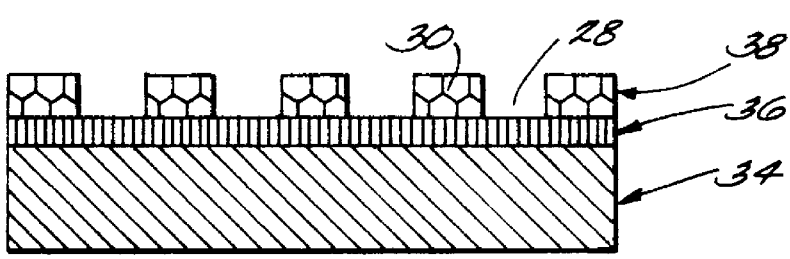

After the prebake, the etchable samples (see FIG. 6B) were coated with a positive photoresits 40, like Shipley 1400-31 positive photoresist. With a positive mask 32P (as shown in FIGS. 4) in place (see FIG. 6C), the polyimide film 38 is wet etched (50 sec. E422). The etching removes film 38 in the open regions of the positive mask 32P, while leaving film 38 in the closed regions of the mask 32P. This forms the holes 28 and strands 30 in the polyimide 38 (as FIG. 6D shows). The etched film is rinsed (15 sec. deionized water (DI)), and spun dry (30 sec. nitrogen), and the photoresist stripped away (2 min S420) (as FIG. 6E shows).

Figure 5C:
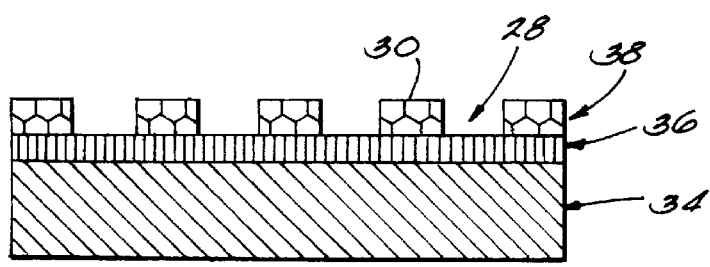

The photosensitive polyimide samples (see FIG. 5B) were exposed, with the negative mask 32N (shown in FIGS. 3A/B) in place, to polyimide lithography on a Karl Suss MJB 3 mask aligner, and then spray developed, overlapped (consists of simultaneous spraying with developer and rinse), and rinsed (see FIG. 5C).

Curing of the polyimides (both etchable and photosensitive) was performed in a nitrogen purged programmable furnace (Fisher, Model 495A, Pittsburgh, Pa.). Flowing nitrogen at about 50 SCFH reduces the oxygen content of the furnace to about 5%, thus reducing oxidation of the films. The samples were allowed to cool to 100° C. before removal from the furnace.

The strength of the film is considerably reduced, if not cured in an unpurged furnace. This is due to oxidation of the polyimide during cure. All of the polyimides become qualitatively "brittle" if cured in normal atmospheric concentrations of oxygen.

The HTR3-100 had the most shrinkage during curing, which resulted in narrower strands. There is an advantage in this because the ideal filament structure is more closely approximated with smaller strands.

Figure 10A:
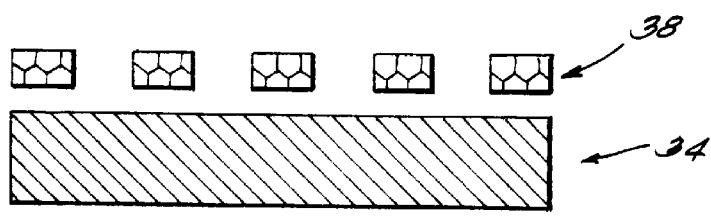
FIGS. 10($a$) to 10($d$) are schematic views of the process of stacking primary and spacer layers to form the multiple layer porous membrane structure shown in FIG. 1.

Following the lithographic treatment and curing, as just described, the films 38 are then removed from the substrate 34 (as FIG. 10A shows). This is accomplished by etching the thermally grown silicon dioxide layer from under the membranes. The films 38 are released from the substrate by immersing the wafers in Transistar™ buffered oxide etchant [6 parts ammonium fluoride:1 part hydrofluoric acid (HF)]. A milliliter or two of concentrated HF (49%) is added to speed up the release process (with added HF the process takes approximately 30 seconds to one minute). The released films were transferred to a petri dish of deionized water with Teflon™ forceps and rinsed for five minutes.

Spacing layers with 50μ diameter holes and 4.5 μm strands were fabricated of two different thicknesses, referred to as thin (having a nominal thickness of 2 μm) and thick (having a nominal thickness of 4 μm). These structures can be identified as 50 μm/4.5 μm/2 μm (hole dimension/strand dimension/thickness) structures and 50 μm/4.5 μm/4 μm structures.

Approximately 100 A of gold was electron beam evaporated onto the single layer samples attached to silicon substrates. Scanning electron microscopy (SEM) was performed in a JEOL JSM-35 scanning electron microscope.

The following Table 1 summarizes measurements made on the single layer structures using a Tencor P1 long scan profiler (Mountain View, Calif.) and SEM cross sections:

TABLE 1

DIMENSIONS OF SINGLE LAYER MICROSTRUCTURE MEMBRANES

| Material | Film Thickness (μm) | | Dimensions Hole/Strand (Nominal) | |
|---|---|---|---|---|
| Thin | | 6/2.8 (μm) | 10/2 (μm) | 50/4.5 (μm) |
| U7501 | 2.5 (SEM) | 2 | 2 | 4 |
|  | 2.7 (Profiler) | | | |
| U4212 | 2 | 1 | 1.5 | 3 |
| HTR3-100 (Depending upon Processing) | 1.5–1.8 (SEM) 1.3–1.75 (Profiler) | 1.3 | 1.25 | 3 |
| Thick | | | | |
| U7501 (Depending upon Processing) | 5.7 (SEM) 5.4–6.8 (Profiler) | | | |
| U4212 | 3.9 (SEM) 4 (Profiler) | | | |
| HTR3-100 | 3.4 (SEM) 3 (Profiler) | | | |

Figure 7A:
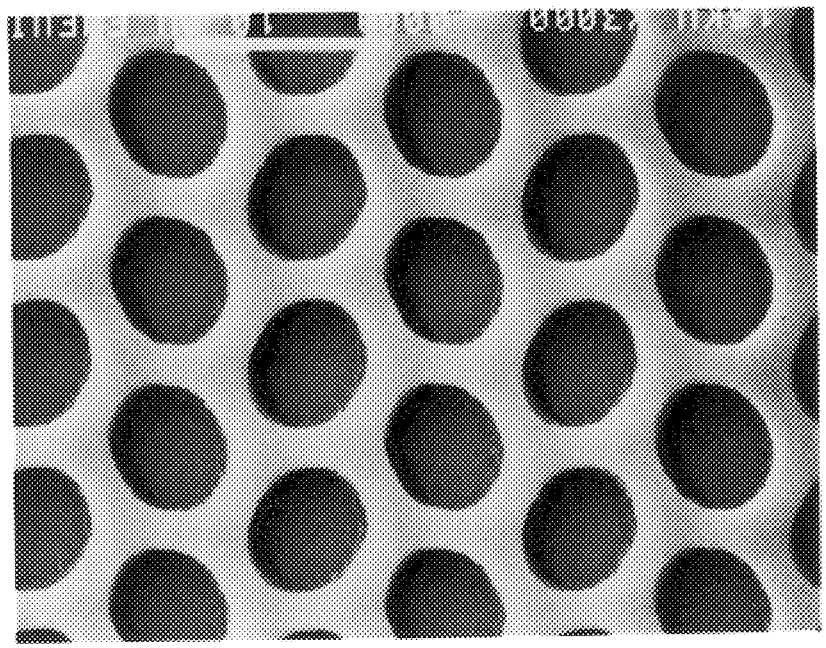
FIGS. 7($a$) to 7($d$) show scanning electron micrographs of primary film layers (U7501, U4212, and HTR3-100 polyimides) patterned with 6.2 $\mu$m openings and 2.8 $\mu$m strands (still attached to the silicon substrate used in microfabricating the films)
Figure 7B:
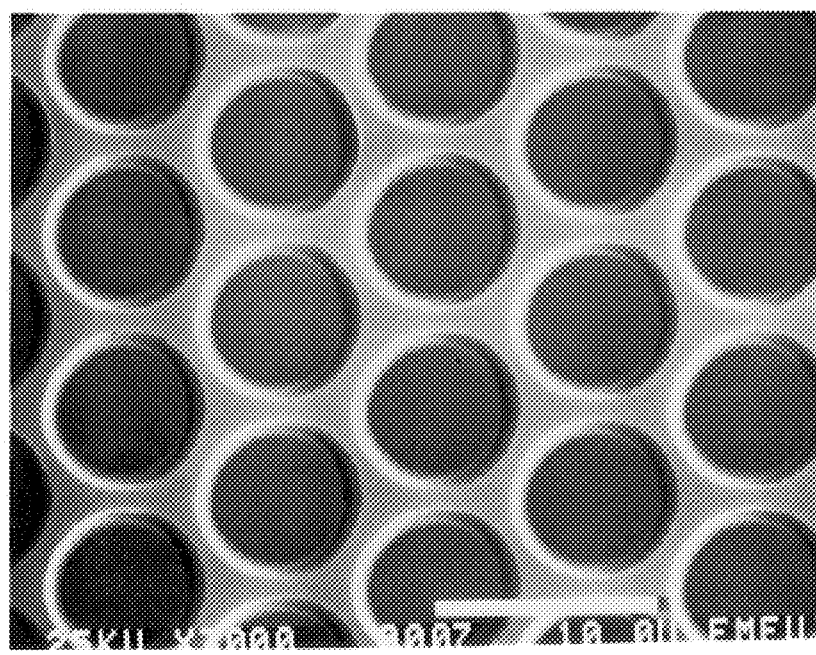
Figure 7C:
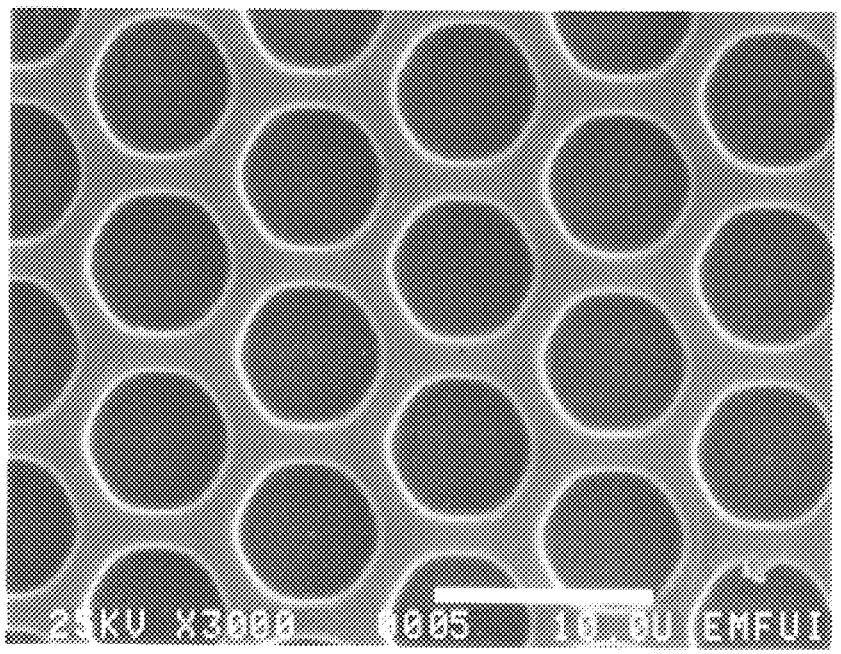
Figure 7D:
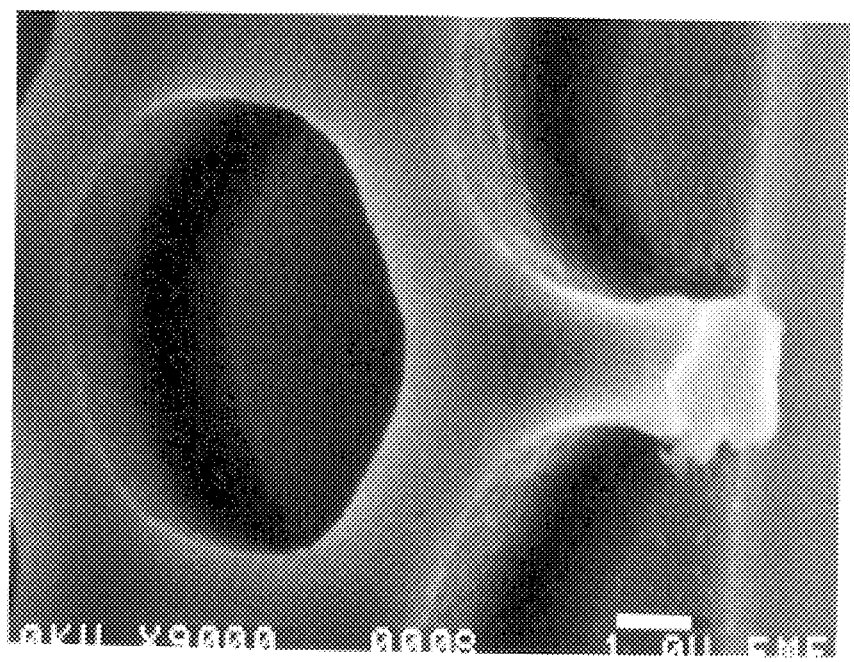

FIGS. 7A/B/C/D show scanning electron micrographs of the top surface of single layer films patterned with the mask with 6.2 μm openings and 2.8 μm strands (still attached to the silicon substrate). FIG. 7A shows a single microfabricated film layer made from U7501 material. FIG. 7B shows a single microfabricated film layer made from U4212 material. FIG. 7C shows a single microfabricated film layer made from HTR3-100 material. FIG. 7D shows an enlarged, slightly angled view of a hole formed in the single layer film of U7501 material.

Figure 8A:
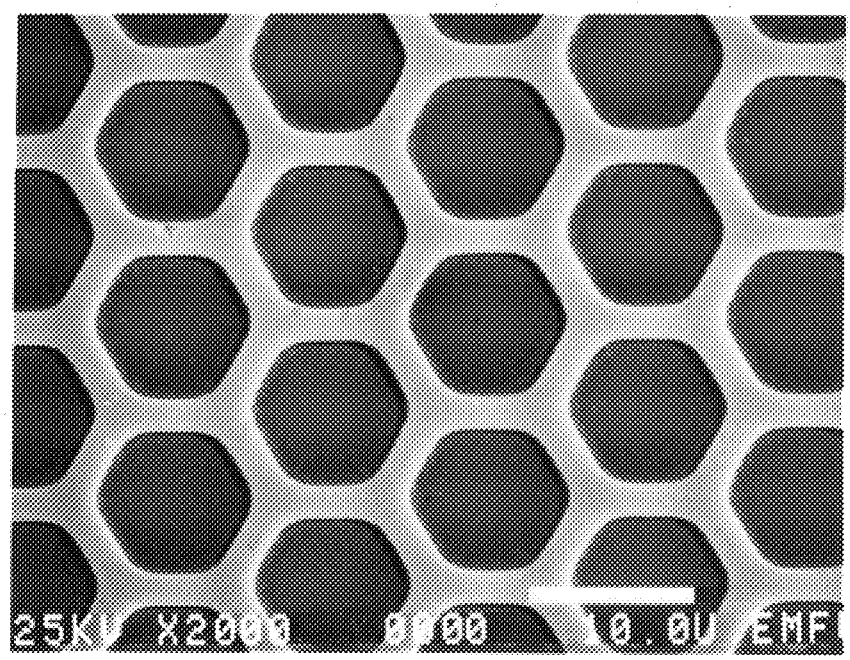
FIGS. 8($a$) to 8($d$) show scanning electron micrographs of primary film layers (U7501, U4212, and HTR3-100 polyimides) patterned with 10 $\mu$m spaces and 2 $\mu$m strands (still attached to the silicon substrate used in fabricating the films)
Figure 8B:
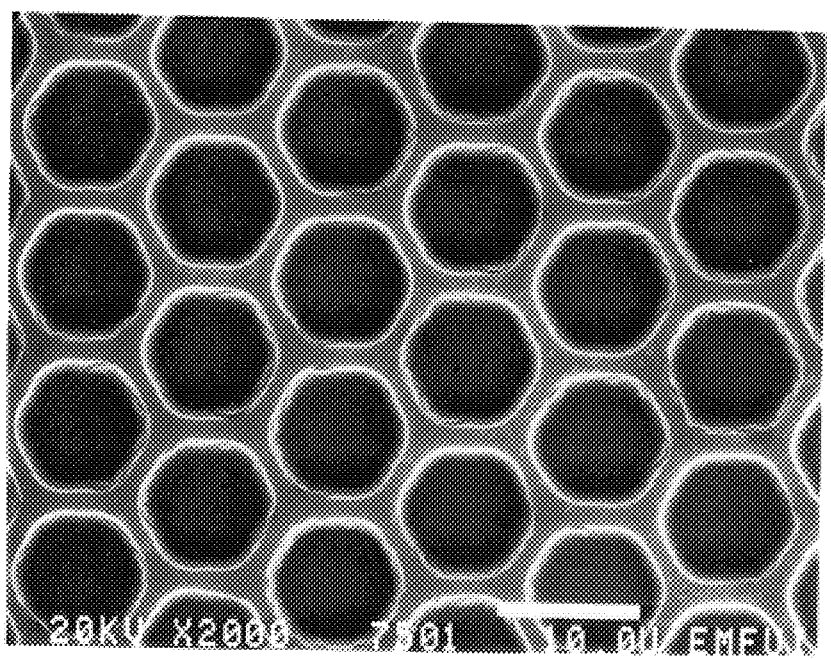
Figure 8C:
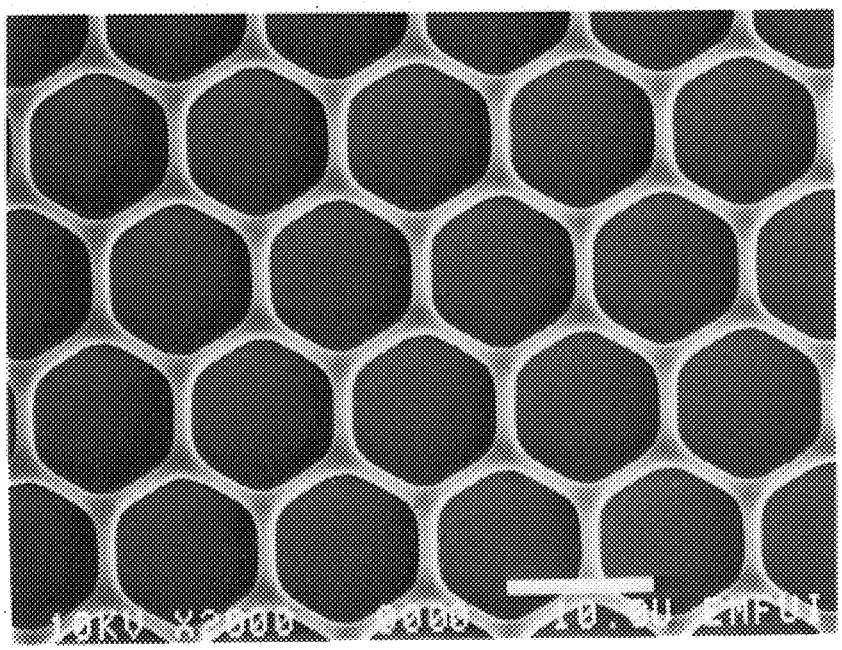
Figure 8D:
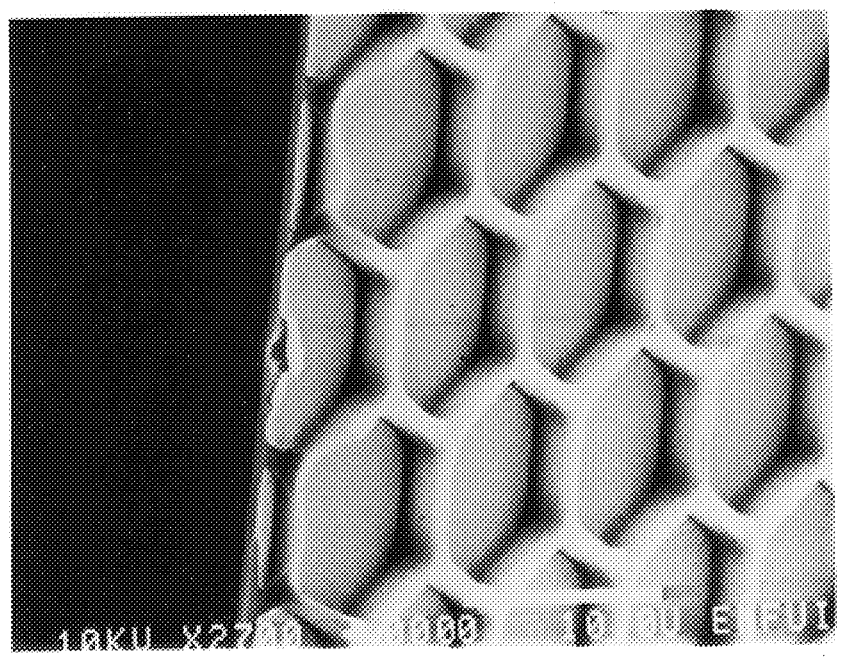

FIGS. 8A/B/C/D show scanning electron micrographs of the top surface of films patterned with 10 μm spaces and 2 μm strands (still attached to the silicon substrate). FIG. 8A shows a single microfabricated film layer made from U7501 material. FIG. 8B shows a single microfabricated film layer made from U4212 material. FIG. 8C shows a single microfabricated film layer made from HTR3-100 material. FIG. 8D shows an enlarged, slightly angled view of holes formed in the single layer film of HTR3-100 material.

Figure 9A:
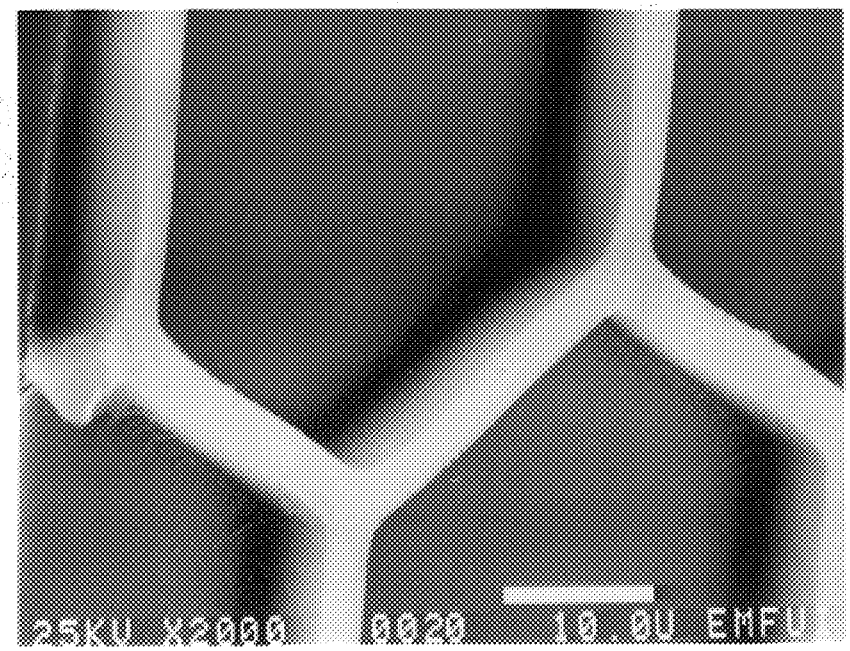
FIGS. 9($a$) to 9($d$) show scanning electron micrographs of spacer film layers (U7501, U4212, and HTR3-100 polyimides) patterned with 50 $\mu$m holes and 4.5 $\mu$m strands (with a thickness of the 4 $\mu$m) (still attached to the silicon substrate used in fabricating the films)
Figure 9B:
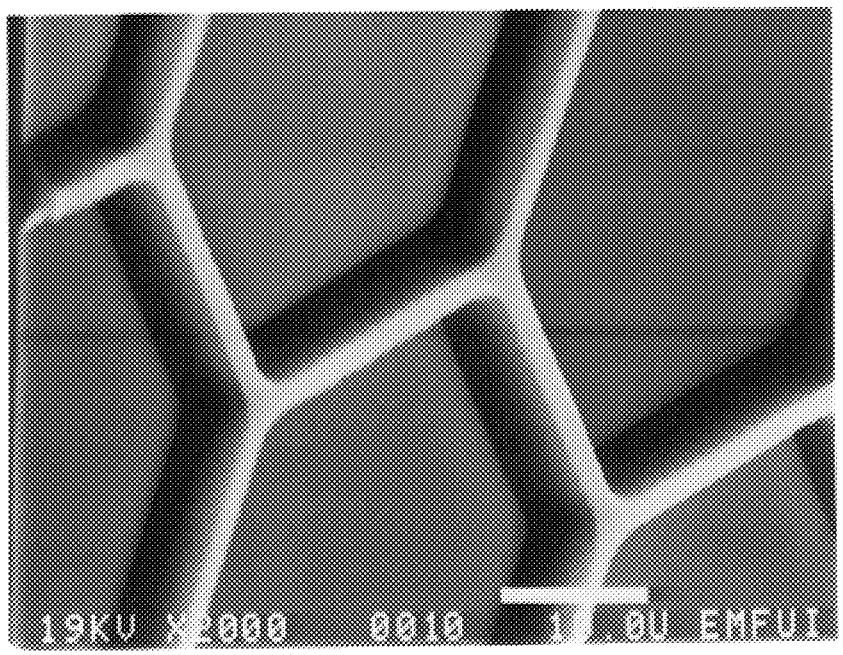
Figure 9C:
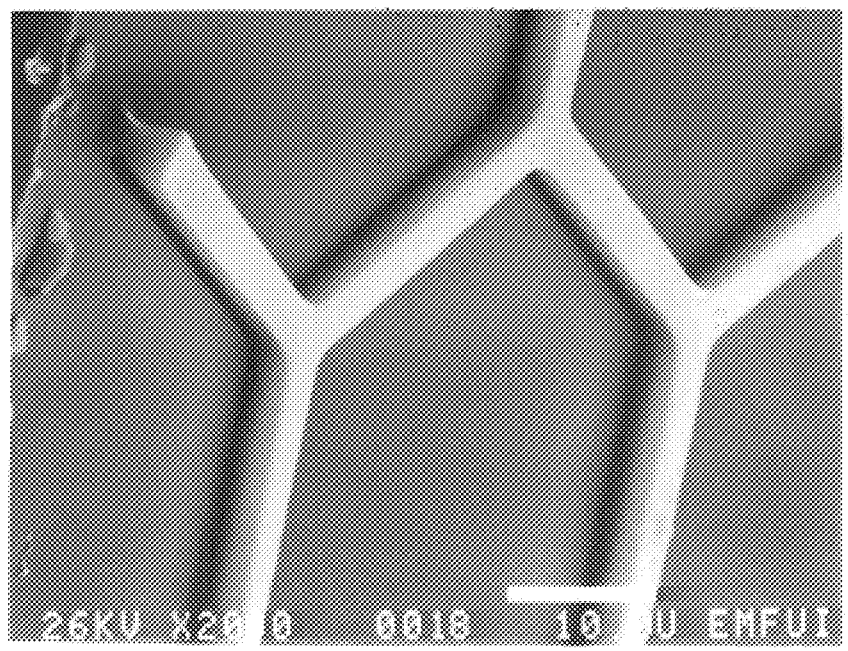
Figure 9D:

FIGS. 9A/B/C/D show scanning electron micrographs of the top surface of single layer films patterned with the mask with 50 μm holes and 4.5 μm strands (with a thickness of the 4 μm) (still attached to the silicon substrate). FIG. 9A shows a single microfabricated film layer made from U7501 material (at a slightly angled view). FIG. 9B shows a single microfabricated film layer made from U4212 material (at a slightly angled view). FIG. 9C shows a single microfabricated film layer made from HTR3-100 material (at a slightly angled view). FIG. 9D shows cross section of the 4 μm thick film made from U7501 material.

From the micrographs, it can be seen that the films are quite uniform, i.e. the features are consistent from one hole to the next. There was "rounding" of features and other pattern anomalies that occurred, which varied according to film type and may have in large part due to processing variables, such as shrinkage of the film, optical effects due to imperfect contact between the mask plate and the substrate, and over-etching.

For good pattern transfer using a contact printing mask aligner (like the Karl Suss MJB 3), intimate contact between mask and substrate is essential. Given that perfect contact is not possible, there is some light diffraction around the mask edges, and the exposed regions are further separated when this overlap is reduced and pattern transfer is improved. Mask-to- substrate contact is affected by several variables including: the uniformity of the prebaked film, edge bead, particulates, substrate-mask contact pressure, and wafer flatness. Wafer flatness seemed to be one of the most important factors for achieving good yields, i.e. membranes that were completely porous. Wafers which were not flat had incomplete development in the center of the wafer. The wafers were examined by optical interference and this problem was remedied by selecting wafers which had uniform interference fringes.

The thin spacing layers exhibited better pattern transfer than the thick spacing layers, due to absorption of ultraviolet (UV) light by the top of the thicker film causing the bottom of the film to be more soluble upon development.

Still, overall, the dimensions seen in the scanning electron micrographs are close to those specified in the mask design.

B. Stacking the Microfabricated Film Layers

Multilayer microstructure membranes are made consisting of either alternating films of large and small dimensions or of all the same dimensions. In all cases like materials were assembled.

Figure 10B:
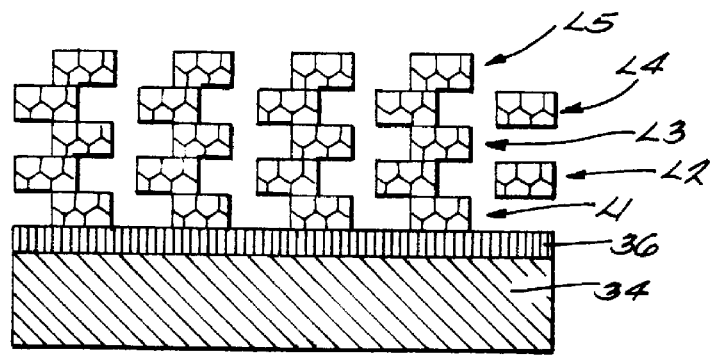

In making the multiple structure membranes, released membranes of like polyimide material were stacked together and laminated to a polyester webbing to provide good mechanical integrity of the membranes. FIG. 10 shows the process, which can be summarized as follows:

(1) a drop of water was placed on top of an unreleased film;

(2) a free membrane was then transported onto the drop of water using a vacuum pickup fitted with a Teflon tip;

(3) the film was positioned with the vacuum pickup on a silicon substrate 34 (as before described with an oxide coating 36, as FIG. 10B shows), and flattened by gently blowing with a nitrogen gun, while simultaneously applying suction at the corner of the film;

(4) a Ultrasonic Wire Bonder (West Bond, Model 7700A-45-66, Anaheim, Calif.) was used to tack multiple layers (designated L1, L2, etc. in FIG. 10B) of the films together around the perimeter, if necessary, to the substrate 34. The U7501 sometimes required this step, the U4212 always needed bonding and the HTR3-100 never needed bonding. The layers L1; L3; and L5 comprise film with the smaller diameter holes 28 and smaller strands 30 (for example, a 10 $\mu$m/2 $\mu$m film structure, already described). The alternating layers L2 and L4, which are sandwiched by the other layers, comprise the spacer layers with the larger diameter holes and larger strands (for example, the 50 $\mu$m/4.5 $\mu$m/2 $\mu$m or 50 $\mu$m/4.5 $\mu$m/4 $\mu$m structures, already described.)

Figure 10C:
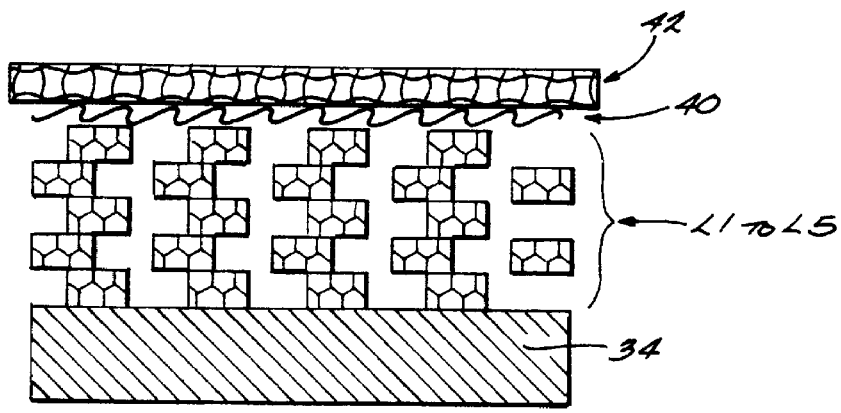
Figure 10D:
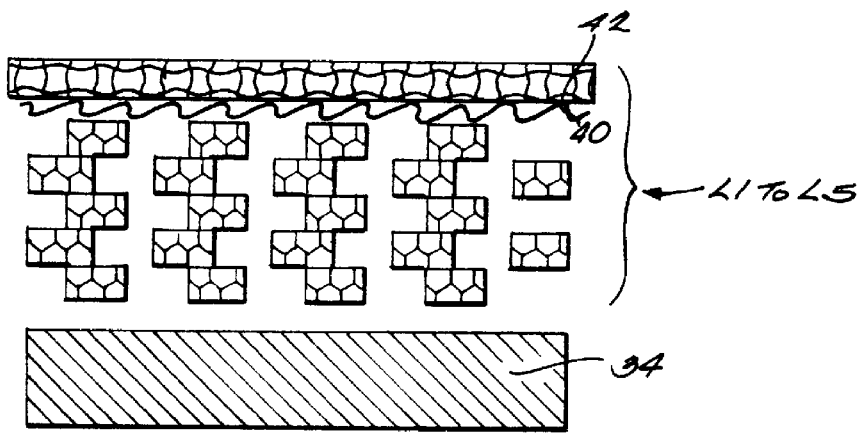

(5) the films were cured again under the conditions described before;

(6) an interpenetrating, stranded network 40 of molten ethylene vinyl acetate (EVA) was formed on the surface of the samples, 40–50 strands per inch (as FIG. 10C shows);

(7) next, a layer of polyester webbing 42 was clamped to the exterior surface (as FIG. 10C also shows);

(8) the samples were baked at 80° C. for 10 minutes to remove the solvent (toluene) from the EVA;

(9) finally, the same oxide etching process as described above was performed to remove the laminated membranes (as FIG. D shows);

(10) membranes were mounted in titanium rings 0.5 inches in diameter (like those shown in FIGS. 1A/B/C);

(11) the assembled multiple layer membrane structures were stored in 70% ethyl alcohol to sterilize them.

This process was performed for films with the same dimensions, as well as stacking alternating layers of different dimensions. In addition, single layer films were laminated to 5 um Goretex™ membranes, which were used as controls.

The following Table 2 lists the types of multilayer structures made:

TABLE 2

DIMENSIONS OF MULTILAYER MICROSTRUCTURE MEMBRANES

| Material | Primary Layer (Hole/Strand) | Nominal Sizes ($\mu$m) Spacer Layer Hole/Strand/Thick | Total Number of Layers |
| --- | --- | --- | --- |
| Multiple Identical Layers | | | |
| U7501 | 6/2.8 | None | 2 |
| U7501 | 6/2.8 | None | 4 |
| U4212 | 6/2.8 | None | 2 |
| U4212 | 6/2.8 | None | 4 |
| U4212 | 10/2 | None | 3 |
| HTR3-100 | 10/2 | None | 3 |
| HTR3-100 | 10/2 | None | 4 |
| HTR3-100 | 10/2 | None | 6 |
| Alternating Layers | | | |
| U7501 | 10/2 | 50/4.5/2 (thin) | 5 |
| U7501 | 10/2 | 50/4.5/4 (thick) | 5 |
| U4212 | 10/2 | 50/4.5/2 (thin) | 5 |
| U4212 | 10/2 | 50/4.5/4 (thick) | 5 |
| HTR3-100 | 10/2 | 50/4.5/2 (thin) | 5 |
| HTR3-100 | 10/2 | 50/4.5/4 thick | 5 |

Figure 11A:
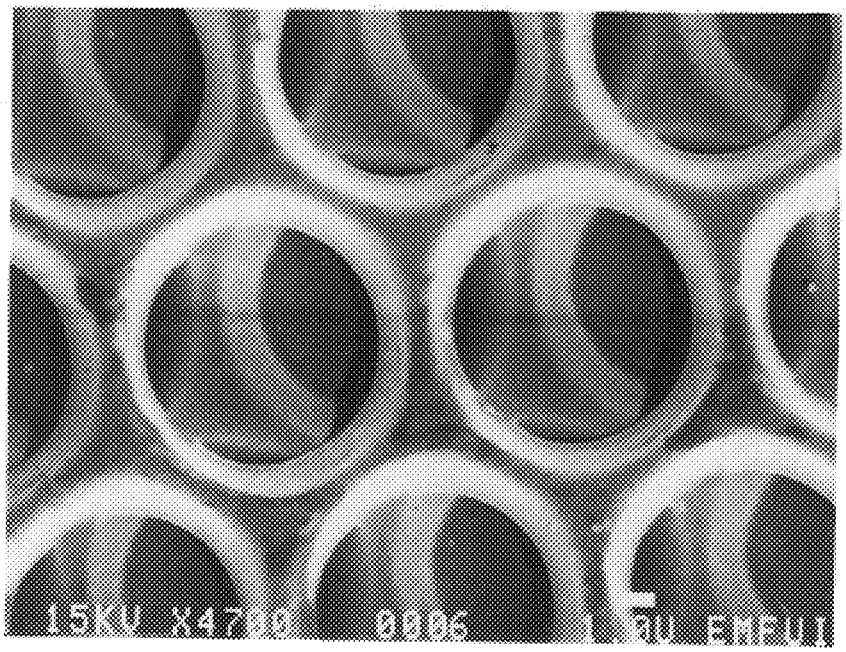
FIGS. 11($a$) to 11($b$) show scanning electron micrographs of multiple 3- layer stacked membrane structures (U4212 and HTR3-100 polyimides) that embody the features of the invention.
Figure 11B:
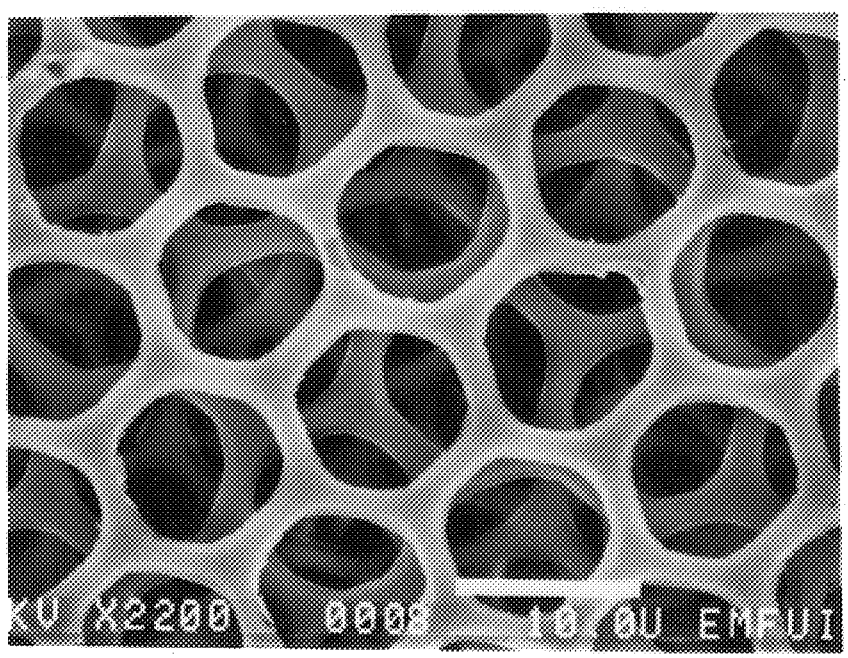

FIG. 11A shows a scanning electron micrograph of a representative example of the three layer stacked structure of the U4212 membrane. The excessive rounding of the features is due to a slight over-etch. In addition, at some points of contact the two layers seem to have "melted" together during the post stacking cure. FIG. 11B shows a scanning electron micrograph of the six layer stacked structure of HTR3-100 membrane. Little alignment is apparent from one layer to the next. The manual stacking and curing of the films results in a random alignment between the layers.

Figure 12A:
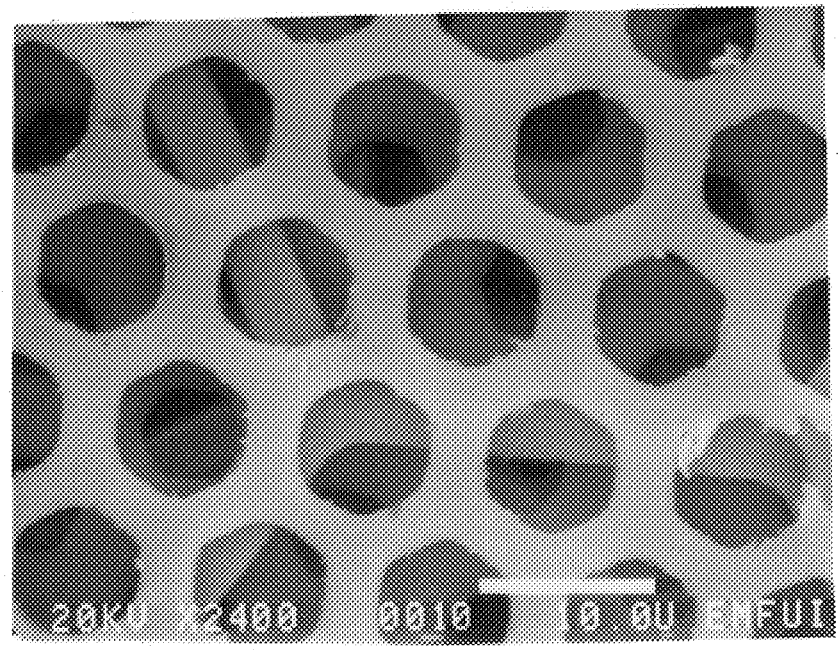
FIGS. 12($a$) to 12($c$) show scanning micrographs of multiple 5- layers stacked membrane structures (U7501, U4212, and HTR3-100 polyimides) that embody the features of the invention.
Figure 12B:
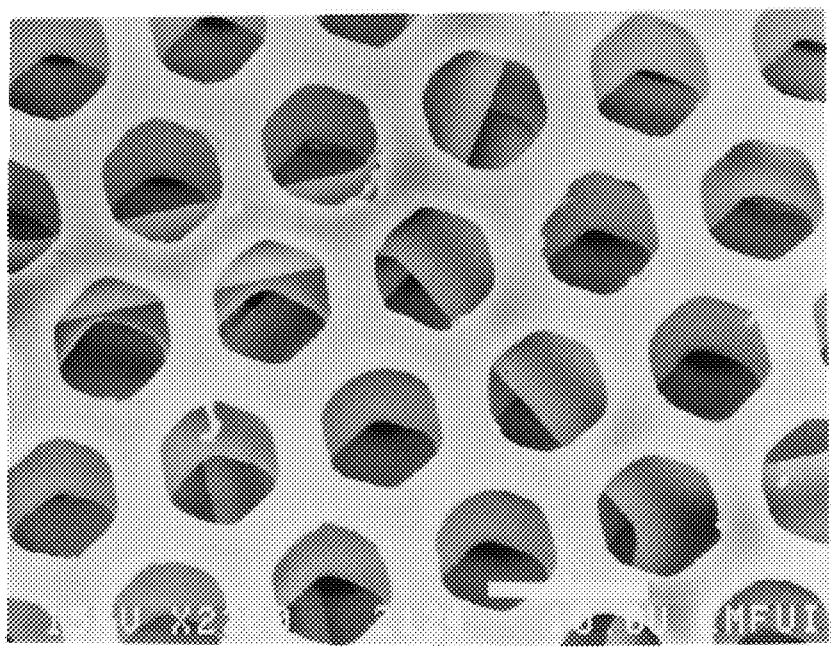
Figure 12C:
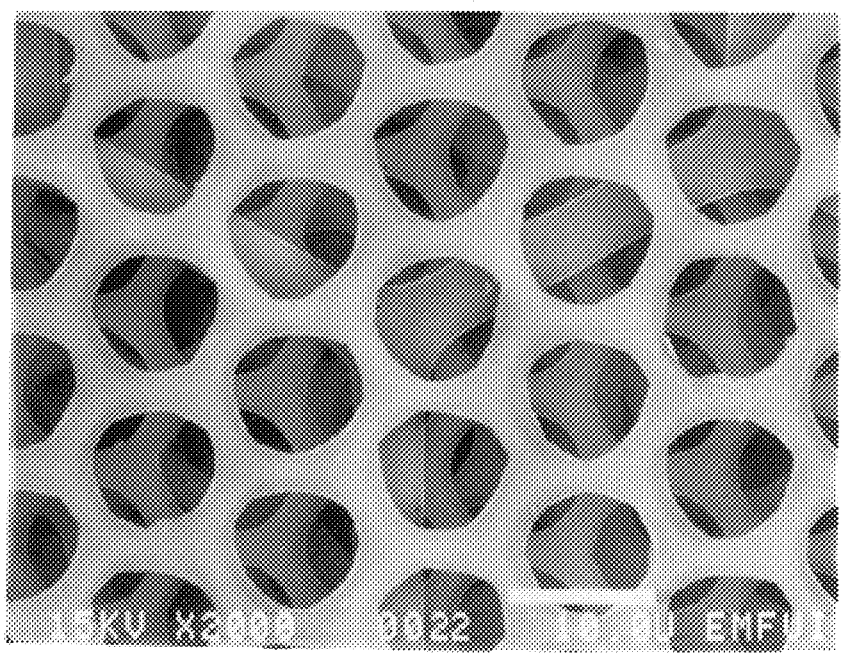

FIGS. 12A/B/C show micrographs of the membranes comprising alternating 5 layers of film layers and the thick spacer layers (4 $\mu$m), for each of the three polyimides used. FIG. 12A shows the spacer-stacked U7501 structure. FIG. 12B shows the spacer-stacked U4212 structure. FIG. 12C shows the spacer-stacked HTR3-100 structure. In each case all five layers can be seen. Again, a random alignment is observed between the layers. The strand in the spacer layer can be seen to partially block a hole in the membrane surface.

Figure 13A:
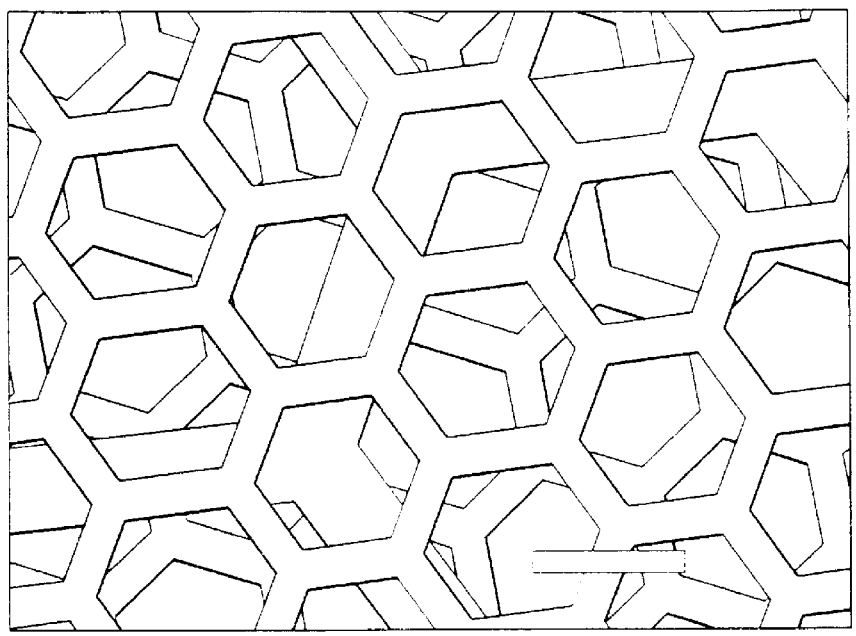
FIGS. 13($a$) to 13($b$) show scanning electron micrograph of other multilayer stacked membrane structures (U4212 polyimide) that embody the features of the invention.
Figure 13B:
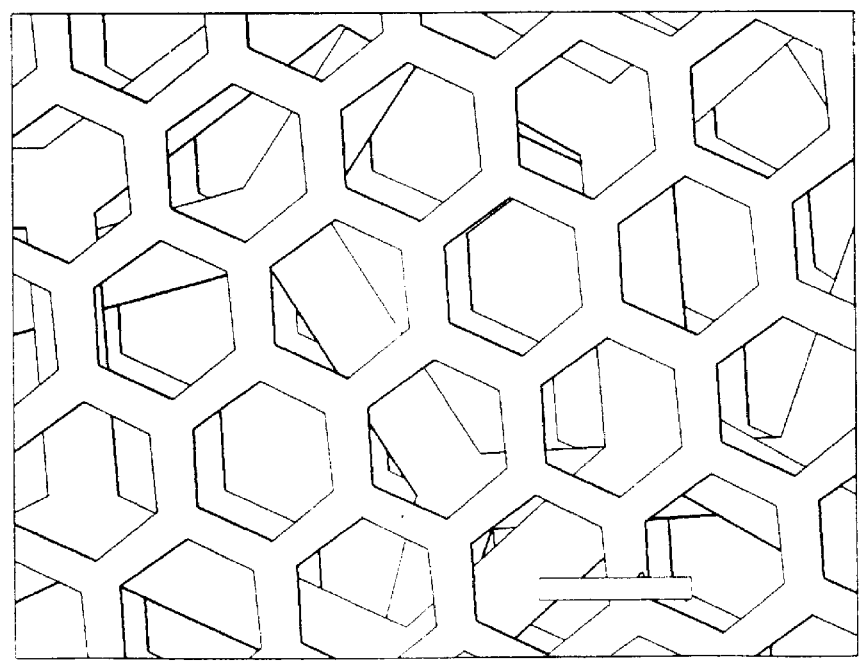

FIGS. 13A/B show scanning electron micrograph of other multilayer membrane structures made in the manner described above. In FIGS. 13A/B, the structures alternate one polyimide film layer (U4212 material) microfabricated with 15 $\mu$m hexagonal holes with strands of 2 $\mu$m (2 $\mu$m thick) with a second polyimide film layer (also U4212 material) microfabricated with 50 $\mu$m hexagonal holes with strands of 4.5 $\mu$m (3.5 $\mu$m thick), used as a spacing layer. FIG. 13A shows the presence of one 50 $\mu$m/4.5 $\mu$m/3.5 $\mu$m spacing layer sandwiched between two 15 µm/2 µm/2 µm layers. FIG. 13B shows alternate layering of three 15 µm layers and two 50 µm spacing layers. As before, a random alignment of holes and strands is shown. The 50 µm middle spacing layer can be clearly seen in FIGS. 13A and B under the top 15 µm layer.

Manual stacking of the layers therefore produces no particular uniform alignment, and it is believed that no such uniform alignment is preferred. Since the holes of the spacing layers are much larger than the holes of the primary layers, the smaller holes in the primary layers are not completely blocked by the strands of the spacing layers, thereby providing an open interior architecture that allows inflammatory cells to enter and promote the desired vascularizing effect near the interface with host tissue.

With the addition of a spacer layer, a highly porous structure results. The porosity of the films varied from 50% to 85%.

The film bonding was analyzed qualitatively for all three polyimides as alternating layer membranes. Three test were performed (1) flowing DI water, (2) flowing nitrogen (20 PSI), and (3) wafer breaking. The results of these test were either to pass or fail, which was indicated by delamination. All the multilayer structures passed the first two tests. The spacer-stacked U4212 passed the third test. Delamination of some spacer-stacked U7501 structures and all spacer-stacked HTR3-100 structures during implanting was also observed. This indicates that the adhesion was marginally better for the U4212 material.

It is clearly evident that the membranes display repeatable geometries. Throughout the handling process all the membranes displayed excellent mechanical stability considering they were about 1.75–6.8 µm thick and had a porosity in the range 50–95%.

Processing photoimageable polyimide can be done in a single lithography step in the same way as for a negative photoresist. Etchable polyimide fabrication, although somewhat more complicated, still requires only a single masking step. After patterning the polyimide film, the area of any flat surface can be identified easily using scanning electron microscopy, and film thicknesses can be measured on a profiler. Fully cured polyimides have excellent physical and thermal properties including: high tensile strength, large Young's modulus of elasticity, large percent elongation at break, a high glass transition temperature, and resistance to many acids and organic solvents.

Brauker et al. have demonstrated that membranes that did have close vascular structures allowed cellular penetration and had pores that were formed by membrane structures (strands or fibers) with a diameter of less than 5 µm, whereas membranes that did not develop close vascular structures had cavities with "plate-like" qualities, having diameters greater than 5 µm. Histological examination of the vascularizing membranes revealed that the invading cells had a rounded morphology, while the cells were flattened in the membranes that did not have close vascular structures. The cells appear to be "trapped" and not allowed to flatten on any surface, which apparently causes the more rounded morphology of the cells which infiltrate the vascularizing membranes. The hypothesis is that the membrane architecture dictates cellular morphology, and the rounded cells in turn secrete some, as yet unknown, trophic factors which promote the formation of vascular structures.

The multilayer, stacked polyimide microfabricated membrane structures made in accordance with the invention provide the type of structure characterized by Brauker et al. The alternating layers of primary and spacer layers increased the porosity of the films, decreasing the opportunity of two strands to coincide in the vertical plane, and increasing the internal volume of the membrane. Cellular penetration with rounded morphology and close vascular structures may noticeably increase for these spacer-stacked membrane structures.

Various features of the invention are set forth in the following claims.

We claim:

1. A material comprising a porous structure forming a chamber to hold living cells while implanted in host tissue, the structure including multiple layers of microfabricated polyimide wherein one layer has a first microfabricated geometric pattern comprising holes having a cross section of greater than about 20 µm and intermediate strands having a dimension less than about 5 µm, and at least one other layer having microfabricated geometric patterns comprising holes having a cross dimension equal to or less than about 20 µm and intermediate strands having a dimension less than about 5 µm.

2. A material according to claim 1 and further including living cells in the chamber.

* * * * *